United States Patent
Shirasaki et al.

(10) Patent No.: US 7,182,732 B2
(45) Date of Patent: Feb. 27, 2007

(54) BLOOD PRESSURE METER CUFF

(75) Inventors: Osamu Shirasaki, Amagasaki (JP); Yoshihiko Sano, Kyoto (JP); Toshio Ohtani, Kyoto (JP); Tomonori Inoue, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/360,410

(22) Filed: Feb. 24, 2006

(65) Prior Publication Data

US 2006/0149153 A1 Jul. 6, 2006

Related U.S. Application Data

(63) Continuation of application No. 10/751,652, filed on Jan. 6, 2004, now abandoned.

(30) Foreign Application Priority Data

Jan. 15, 2003 (JP) ................... 2003-7387

(51) Int. Cl.
*A61B 5/00* (2006.01)
*A61B 5/02* (2006.01)

(52) U.S. Cl. .............. 600/485; 600/490; 600/500

(58) Field of Classification Search .............. None
See application file for complete search history.

(56) References Cited

U.S. PATENT DOCUMENTS

| | | | |
|---|---|---|---|
| 4,938,226 A | 7/1990 | Danielsson | |
| 6,231,517 B1 | 5/2001 | Forstner | |
| 6,314,058 B1 | 11/2001 | Lee | |
| 6,336,901 B1 | 1/2002 | Itonaga | |
| 6,514,212 B1 | 2/2003 | Ide | |

(Continued)

FOREIGN PATENT DOCUMENTS

CN 1277006 A 12/2000

(Continued)

OTHER PUBLICATIONS

Alexander, H. et al. (1977). "Criteria in the Choice of an Occluding Cuff for the Indirect Measurement of Blood Pressure," *Medical & Biological Engineering & Computing*, UK, issued by *Institution of Electrical Engineers* 15:2-10.

*Primary Examiner*—Robert L. Nasser
(74) *Attorney, Agent, or Firm*—Morrison & Foerster LLP

(57) ABSTRACT

Provide is a blood pressure meter cuff capable of avoiding an influence of an edge effect by pressurizing only a portion of a blood vessel in the downward vicinity of the body surface to thereby measure a correct blood pressure. A blood pressure meter cuff 1 includes: a fluid bag into which a fluid is injected; and a fixing tool fixing the fluid bag on a limb of a human body or the like, wherein a width in the axial direction of the limb, of the fluid bag is a value suitable for selectively pressurizing only a portion of a blood vessel present in the downward vicinity of the skin. In a case where pressurization is imposed on only a portion of the radial artery present in the downward vicinity of the body surface and adjacent to a radial styloid process of a wrist, a width, in the axial direction of a limb, of the fluid bag is set to 15 mm or more and 25 mm or less.

4 Claims, 5 Drawing Sheets

U.S. PATENT DOCUMENTS

| | | |
|---|---|---|
| 2002/0077558 A1 | 6/2002 | Itonaga |
| 2002/0095092 A1 | 7/2002 | Kondo |
| 2002/0188209 A1 | 12/2002 | Ogura |

FOREIGN PATENT DOCUMENTS

| | | |
|---|---|---|
| EP | 1212979 A2 | 12/2002 |
| FR | 616801 A3 | 12/1978 |
| JP | 05-31084 A | 2/1993 |
| JP | 06-133938 A | 5/1994 |
| JP | 9-238910 A | 9/1997 |
| JP | 9-285453 A | 11/1997 |
| JP | 2000-512875 A | 10/2000 |
| JP | 2002-191567 A | 7/2002 |
| TW | 326156 U | 2/1998 |
| WO | WO-95/00070 A1 | 1/1995 |

Forearm side

Peripheral side

A　B　C

PRIOR ART

BLOOD PRESSURE METER CUFF

REFERENCE TO RELATED APPLICATIONS

This application is a continuation of Ser. No. 10/751,652, filed Jan. 6, 2004, now abandoned which claims priority to Japanese Application No. 2003-7387, filed Jan. 15, 2003, the disclosures of which are incorporated herein by reference.

BACKGROUND OF THE INVENTION

1. Field of the Invention

The present invention relates to a blood pressure meter cuff equipped with a fluid bag into which a fluid is injected and a fixing tool fixing the fluid bag.

2. Description of the Prior Art

There have been available various kinds of non-invasive blood pressure measuring methods, among which, currently, an oscillometric method (or an oscillation method) is most widely proliferated. The oscillometric method is conducted such that a tourniquet in a belt-like shape called a cuff having a fluid bag therein is fixedly wrapped around a limb and an internal pressure is given to the fluid bag to pressurize an artery in the limb to capture a change in arterial volume determined in a balance between an pressurization pressure as a reaction and a pressure in the artery and estimate a blood pressure value. To be more concrete, since a change in arterial volume is sensed as a change in internal pressure in the fluid bag. (which is a pulse wave) and an amplitude thereof is altered depending on a blood pressure and an pressurization pressure, a blood pressure can be estimated from a change in pulse wave amplitude relative to a pressurization pressure.

While the oscillometric method was developed originally as a method using an arm as a measuring site, commercialization on a blood pressure meter in recent years has proceeded to provide new types measuring a blood pressure at sites other than an arm, such as a wrist and a finger. The new types of blood pressure meters have been increasing a need for themselves on the market because of advantages such as no necessity for taking off clothes in mounting a cuff, which is necessary for an arm type, and a small size and high portability.

Since, especially, a wrist blood pressure meter uses an artery located near an arm as a measuring site, usefulness is generally accepted to be higher than a finger type, though with a convenience at the same level as the wrist type. A cuff of a wrist blood pressure meter is generally mounted at a site in the forearm side adjacent to a wrist joint. According to Alexander H. et al. (see non-patent literature 1), a theory is such that in order to properly pressurize a blood vessel of a limb for measuring a blood pressure, it is required that a width, in an axial direction of a limb, of a fluid bag attached to a cuff in use, that is a cuff width is of 40% or more of a diameter of the limb at a measuring site and blood pressure meters currently on the market are designed according to this theory. Therefore, in a case of a wrist blood pressure meter put into practice, a cuff width is on the order in the range of from 50 to 60 mm.

In actual cases of adopting this kind of cuff, a problem has been arisen to some of users that a pressurization pressure of a fluid bag does not correctly act on a target artery and the target artery is not sufficiently pressurized, therefore disabling a blood pressure to be correctly measured. There are two arteries called the radial artery and the ulnar artery in a wrist and the two arteries each are located in a slightly retreated position surrounded with the two bones called the radius and the ulna and tendons extending in parallel thereto. Hence, a pressurization force of a fluid bag is harder to reach a target artery in the cases than the brachial artery that is an target having been conventionally measured and present in a state where no tendon exists around a bone.

It has been conventionally known that a cuff pressure is not sufficiently transmitted to a blood vessel, in the axial direction of a limb, near both ends of a fluid bag of a cuff of a blood pressure meter to thereby disable the blood vessel to be sufficiently pressurized. This phenomenon is called as an edge effect. If this edge effect occurs, pulsation occurs in a blood pressure in a blood vessel not sufficiently pressurized near an end of a cuff fluid bag. In this case, this pulsation is sensed as a change in cuff pressure, leading to a factor for measurement error if a chance allows.

In order to cancel this problem, a cuff has been conventionally known that pressurizes a wrist joint section easy to be pressurized because an artery is located in the downward vicinity of a body surface. Since, in the wrist joint section, a blood vessel runs outside of the condyle, the blood vessel is located at a shallower position below the skin than a blood vessel in the forearm side, located between the radius and the ulna, the vessel running outside of the condyle is easier to be pressurized. A prominence called the radial (or ulnar) styloid process 32 is present at the peripheral end of the radius (or the ulna) 33, in which portion, especially, a blood vessel 31 is conspicuously present in the downward vicinity of the body surface (see FIG. 6).

The non-patent literature is Alexander H. "Criteria in the choice of an occluding cuff for the indirect measurement of blood pressure," in Medical & Biological Engineering & Computing, (U.K.) issued by Institution of Electrical Engineers, 1977, Vol. 15, pp. 2 to 10).

According to observation by the inventors, it has been found that in a case where a pressure is applied with a cuff having a conventional width on a portion including a site on the body surface in the downward vicinity of which the blood vessel exists, a good result is not necessarily obtained. To be concrete, a phenomenon has been experienced by some of patients that deformation, which is encountered when a blood vessel is not sufficiently pressurized, occurs on a curve of a change in pulse wave amplitude changing depending on a cuff pressure.

Description will be given of a cause for this phenomenon with reference to FIG. 6. It is only around the radial styloid process 32, for example, in a case of the radial artery 31, that a blood vessel is conspicuously present in the downward vicinity of the body surface near the wrist joint and a length of this section is roughly on the order in the range of from 15 to 25 mm. This section is indicated as a section B in FIG. 6. Since a cuff width for a conventional blood pressure meter is, as described above, in the range of from 50 to 60 mm and therefore, a blood pressure 31 is pressurized additionally in sections in the forearm side and the peripheral side adjacent to the section B (the sections A and C of FIG. 6), a change in arterial volume, which is a reaction of the pressurization, that is a pulse wave is also sensed from the blood vessel 31 in the additional sections.

Since the blood vessel 31 is, however, located clearly in deeper positions in the sections A and C than in the section B and surrounded with bones and tendons, the vessel 31 is harder to be pressurized. Therefore, the blood vessel 31 is not occluded even under a pressure which is higher than a blood pressure and so high that the blood vessel is to be occluded by nature. It is thought that the blood vessel. 31 in the sections A and C is in a state lower in cuff pressure than in the section B, that is in a state where a change in arterial volume is not extinct, in other words in a state where the blood vessel 31 is pressurized not to be flat, again in other words, in a state where the edge effect occurs. This hypothesis has been confirmed to be true as a result after the inventors conducted experiments using a transparent cuff and observed pulsation at the upstream and downstream ends of the cuff under a high cuff pressure.

The reason why, though the blood vessel is perfectly occluded at the center of the cuff and a blood flow is blocked, pulsation occurs not only at the upstream end of the cuff, but also at the downstream end thereof, is that the radial artery and the ulnar artery communicate with each other through a thick blood vessel in the palm section more down stream and in a case of a cuff in which only the radial artery is selectively pressurized, a blood flow from the ulnar artery is fed to the cuff down stream end of the radial artery.

If a blood vessel located in the downward vicinity of the body surface is pressurized by a cuff having a fluid bag designed dimensionally in consideration of a relation with a wrist circumference according to the conventional Alexander H. et al.'s theory, an influence from a blood vessel at a site other than a blood vessel in the downward vicinity of the body surface is exerted, leading to a problem to cause a result of an incorrect blood pressure measurement.

SUMMARY OF THE INVENTION

The invention has been made in order to solve the above problem and it is accordingly an object of the invention to provide a blood pressure meter cuff capable of avoiding an influence of an edge effect by pressurizing only a portion of a blood vessel in the downward vicinity of the body surface to thereby measure a correct blood pressure.

A blood pressure meter cuff based on the invention includes: a fluid bag into which a fluid is injected; and a fixing tool fixing the fluid bag on a limb of a human body or the like, wherein a width, in the axial direction of the limb, of the fluid bag is a value suitable for selectively pressurizing only a portion of a blood vessel present in the downward vicinity of the skin.

With the blood pressure meter cuff adopted, it is possible to pressurize only a blood vessel present in the downward vicinity of the skin. As a result, a blood pressure can be correctly measured without receiving an influence of the cuff edge effect.

In the blood pressure meter cuff, a width of the fluid bag is a width suitable for pressurizing a radial artery present in the downward vicinity of the body surface and adjacent to a radial styloid process of a wrist. With such a construction, it is possible to pressurize only a radial artery in the wrist. Thereby, it is possible to provide a wrist blood pressure meter capable of conducting a correct measurement.

A width of the fluid bag is a width suitable for pressurizing a radial artery present in the downward vicinity of the body surface and in an intermediate portion between the radial styloid process of a wrist and the first metacarpal bone base thereof. With such a width of a fluid bag adopted, it is possible to pressurize only the radial artery present in the downward vicinity of the skin in a wrist. Furthermore, by fixedly wrapping a cuff around an intermediate portion between the radial styloid process of a wrist and the first metacarpal bone base, the radial artery and the cuff are hard to be displaced to thereby enable a blood vessel to be stably pressurized. Thereby, it is possible to provide a wrist blood pressure meter capable of measuring a correct blood pressure.

In the blood pressure meter cuff, a width, in the axial direction of a limb, of the fluid bag is preferably 15 mm or more and 25 mm or less. With such a width of a fluid bag adopted, it is possible to provide a blood pressure meter cuff suitable for pressurizing only a portion of a radial artery present in the downward vicinity of the body surface.

DESCRIPTION OF THE PREFERRED EMBODIMENTS

Embodiment 1

Figure 1A:
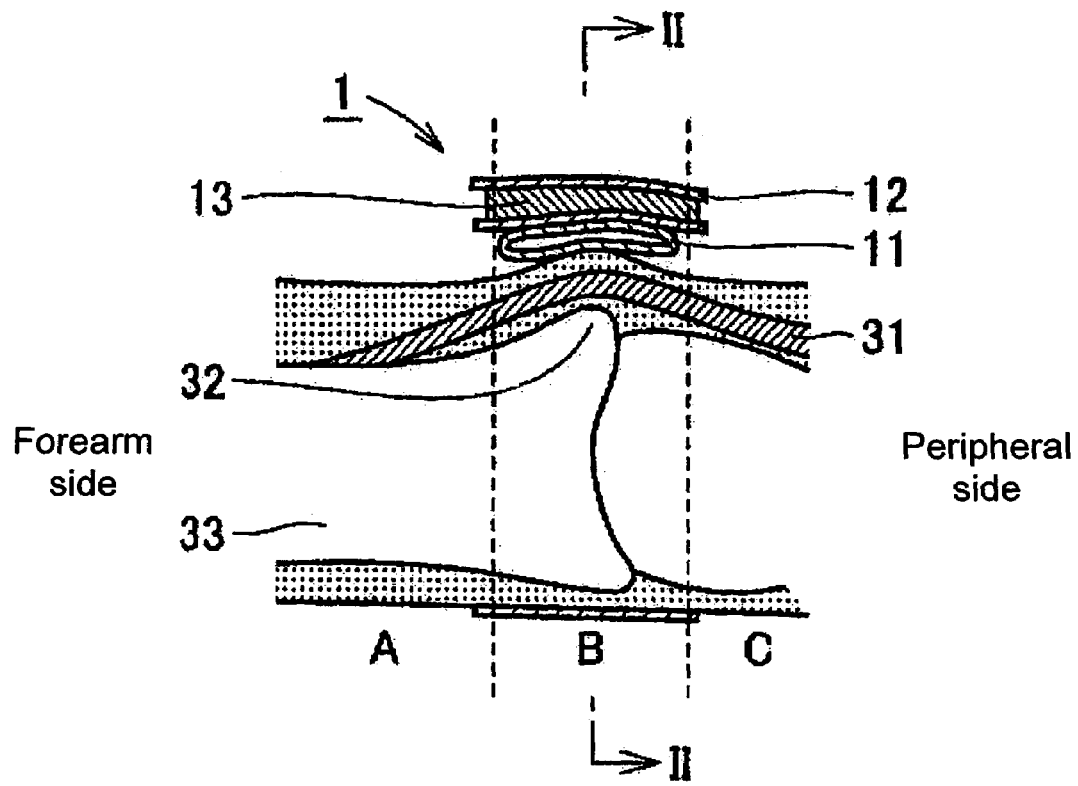
FIGS. 1A and 1B show sectional views of states where a blood pressure meter cuff in a first embodiment based on the invention is mounted on a wrist.
Figure 1B:
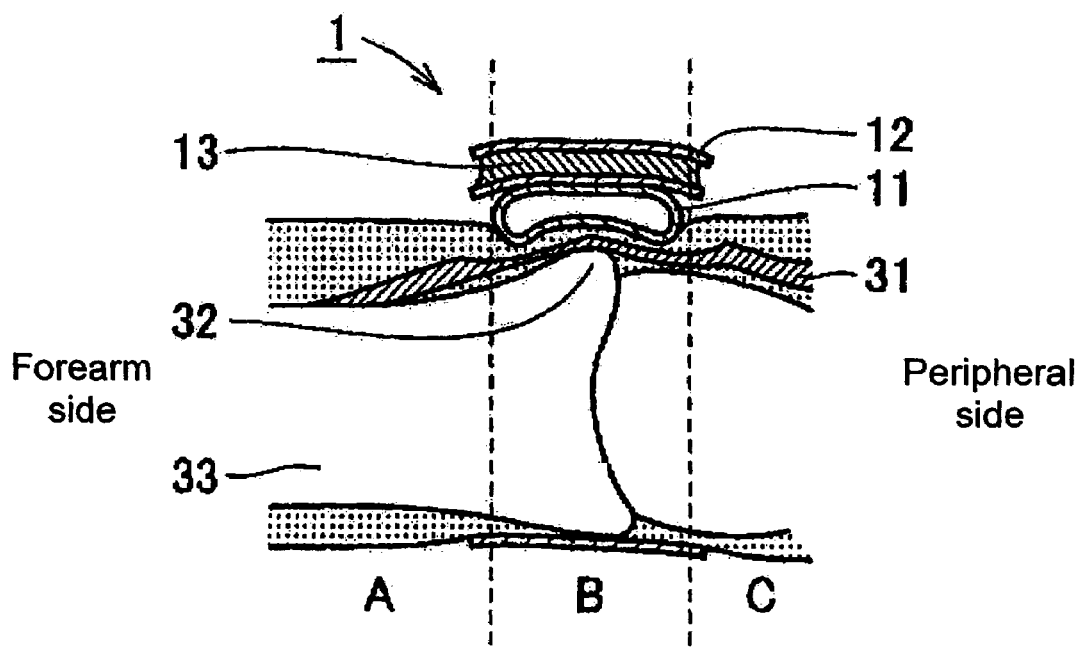
Figure 2:
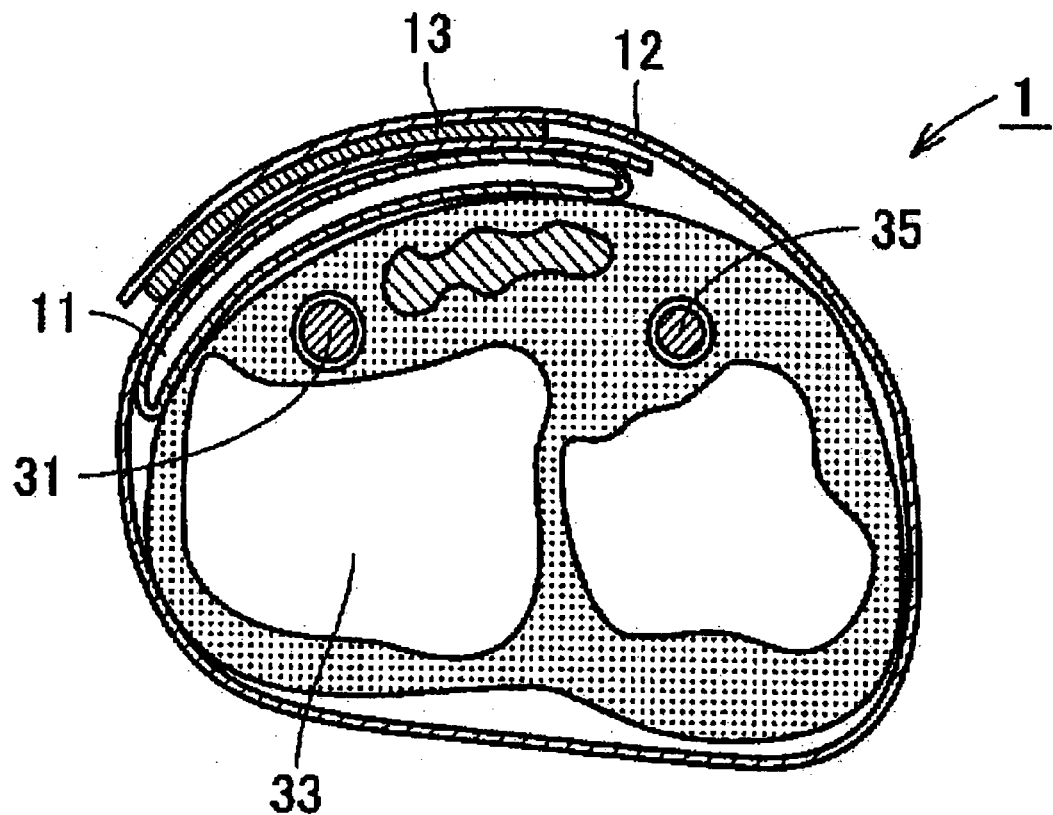
FIG. 2 shows a sectional view taken on line II to II normal to arrows in FIG. 1A showing a state where the blood pressure meter cuff in the first embodiment based on the invention is mounted on a wrist.

Description will be given of a blood pressure meter cuff in this embodiment below with reference to FIGS. 1A and 1B to 4A and 4B. FIGS. 1A and 1B are sectional views showing states where a blood pressure meter cuff in this embodiment is mounted on a wrist, FIG. 2 is a sectional view taken on line II to II normal to arrows in FIG. 1A showing a state where the cuff is mounted on a wrist, FIG. 3 is a top plan view of the cuff in a state where the cuff is extended to be flat and FIGS. 4A and 4B are perspective views showing the cuff in a state where the cuff is mounted on a wrist.

(Structure of Blood Pressure Meter Cuff)

Description will be given of the structure of a blood pressure meter cuff 1 with reference to FIGS. 1A and 1B to 3. The blood pressure meter cuff 1 of this embodiment is used in a wrist blood pressure meter and equipped with a fluid bag 11 into which a fluid such as air is injected and a band 12 as a fixing tool fixing the fluid bag 11 on a wrist.

Figure 3:
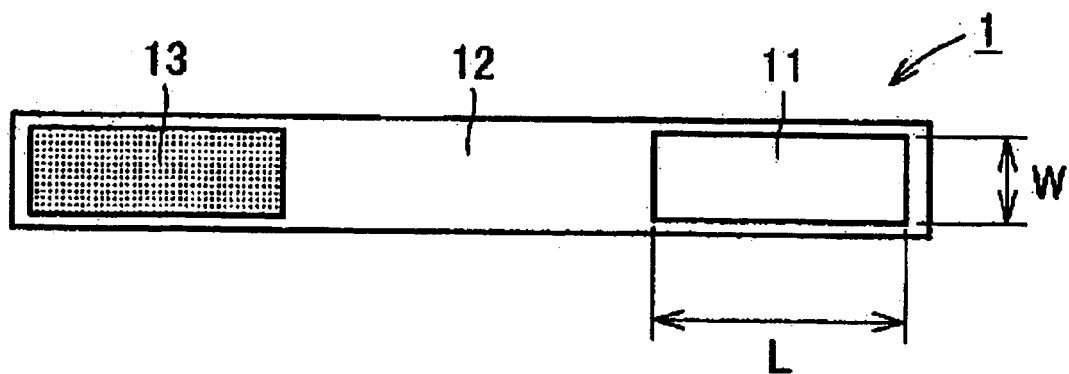
FIG. 3 shows a top plan view of the blood pressure meter cuff in the first embodiment based on the invention in a state where the cuff is extended to be flat.
Figure 4A:
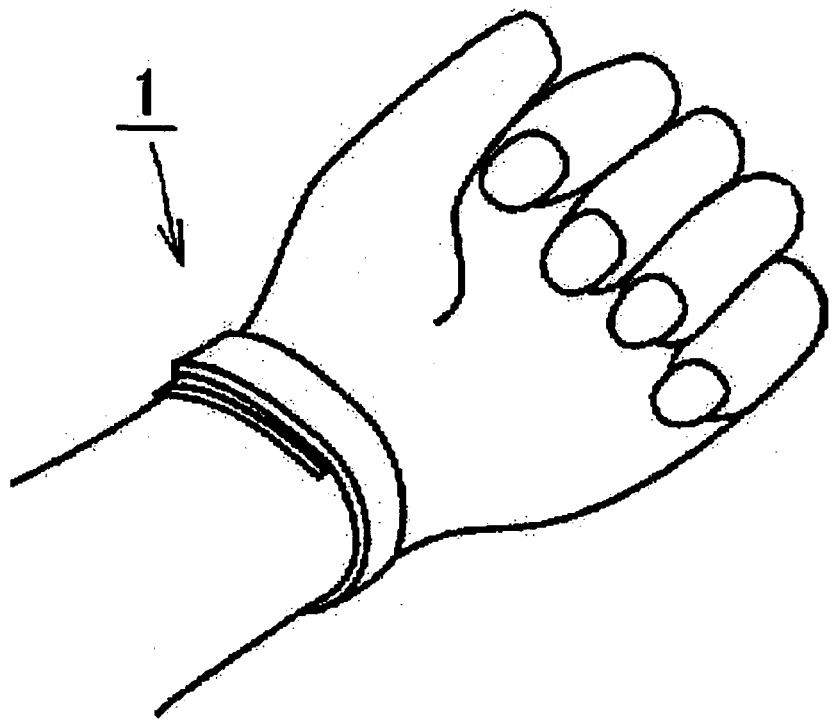
FIGS. 4A and 4B show perspective views of the blood pressure meter cuff in the first embodiment based on the invention in a state where the cuff is mounted on a wrist.
Figure 4B:
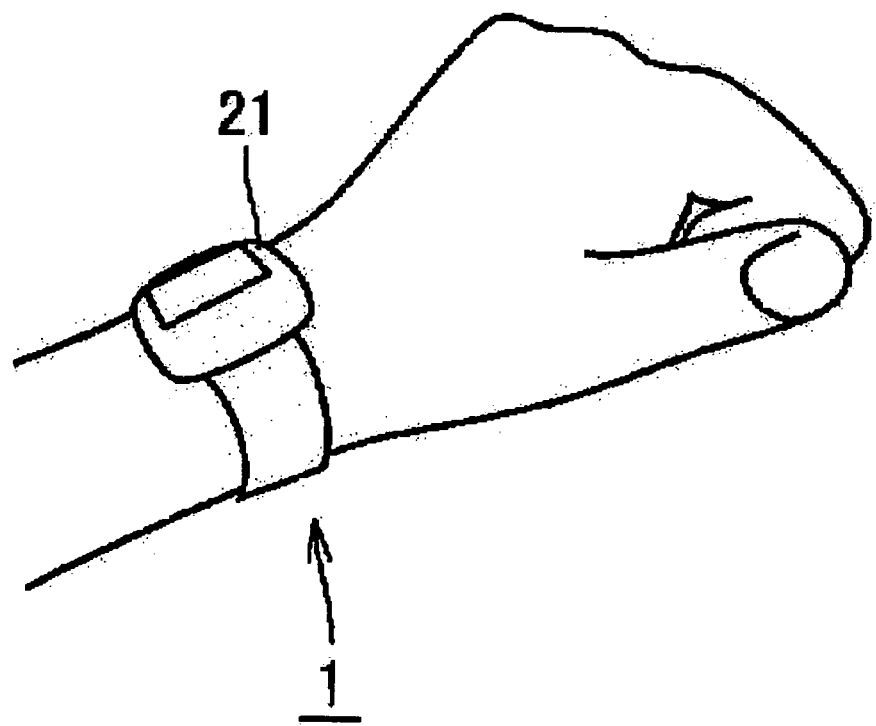

The fluid bag 11 is made of a substance excellent in expandability/contractibility such as a thin film silicone rubber and a latex film and shaped as a rectangle in a top plan view extending in the length direction of the band 12 as shown in FIG. 3. The fluid bag 11 is in a bag like shape as shown in FIGS. 1A and 1B, and FIG. 2, and fed with air thereinto to be inflated.

A width W, in the axial direction of a wrist, of the fluid bag 11 in a state where the bag 11 is wrapped around the wrist is set to a length suitable for selectively pressurizing only a portion of a blood vessel present near the skin in the vicinity of the body surface. In this embodiment, a width of the fluid bag 11 is set to a dimension suitable for pressurizing only a portion of the radial artery 31 adjacent to the radial styloid process 32 and present right under the skin in the vicinity of the body surface (a section B shown in FIG. 1). To be concrete, the width W is 15 mm or more and 25 mm or less. A length L of the fluid bag 11 shown in FIG. 3 is set to a dimension of the order of a value at which the bag 11 pressurizes only the radial artery without pressurizing the ulnar artery 35. (see FIG. 2).

A blood pressure meter body 21 is connected to the fluid bag 11. The blood pressure body 21 is equipped with a built-in pump injecting air as a fluid into the fluid bag 11; a sensor sensing a pressure in the fluid bag 11; and a control device controlling workings of the constituents.

The band 12 fixes the fluid bag 11 on a wrist section and is slightly wider than the width W of the fluid bag 11 as shown in FIG. 3, and has a length of the order of a value at which the wrist section is wrapped around. Hook-loop tape fasteners 13 mutually engaged with each other are provided to both ends, respectively, of the band 12.

(Use Method of Blood Pressure Meter Cuff)

Description will be given of a use method of the blood pressure meter cuff 1 of this embodiment. The cuff 1 of this embodiment is, as shown in FIG. 4, wrapped around a wrist section when being used. At this time, as shown in FIG. 1A, the cuff 1 is mounted so that the fluid bag 11 is brought into contact with a portion of the radial artery 31 adjacent to the radial styloid process 32 of the radius 33 in the downward vicinity of the body surface. Air is fed into the fluid bag 11 from the blood pressure meter body 21 in this state to inflate the fluid bag 11 as shown in FIG. 1B and pressurize a blood vessel.

(Action and Effect)

In this embodiment, since the fluid bag 11 is set to a dimension suitable for pressurizing only the radial artery 31 adjacent to the radial styloid process 32 in the downward vicinity of the body surface, the bag 11 can, as shown in FIG. 1B, pressurize only a blood vessel in the downward vicinity of the body surface. With such a construction adopted, since the fluid bag 11 does not pressurize a portion of a blood vessel that is hard to be pressurized, other than in the downward vicinity of the body surface, thereby enabling avoidance of a malfunction to be caused by sensing pulsation of the blood vessel of the portion hard to be pressurized with the sensor of the flood pressure meter body 21 connected to the fluid bag 11. That is, the edge effect encountered in the use of a conventional fluid bag can be prevented from occurring.

In this embodiment, since a width W of the fluid bag 11 is smaller than conventional, the cuff 1 itself can be smaller. Furthermore, the fluid bag 11 is smaller, a pump feeding air to the fluid bag 11 and the like can be of a smaller capacity, as a result, enabling the blood pressure meter body 21 to be smaller in size. With such constructions combined, the whole of a blood pressure meter can be reduced in size, thereby enabling a blood pressure meter capable of being carried and mounted at all times to be realized.

Furthermore, since the smaller a width W of the fluid bag 11, the smaller a width of the cuff 1, the cuff 1 can be mounted with simplicity and convenience and with certainty. Since the periphery of a wrist joint is located at the base end of a palm, many of people each have a tapered shape of the periphery thereof. Therefore, there has been difficulty mounting a cuff on a wrist fittingly with a larger width as conventional. To the contrary, the cuff 1 of this embodiment is narrow in width to well fit a tapered shape of a wrist, thereby enabling uncertain mounting of a cuff, which is one factor for measurement error, to be prevented.

Embodiment 2

Figure 5:
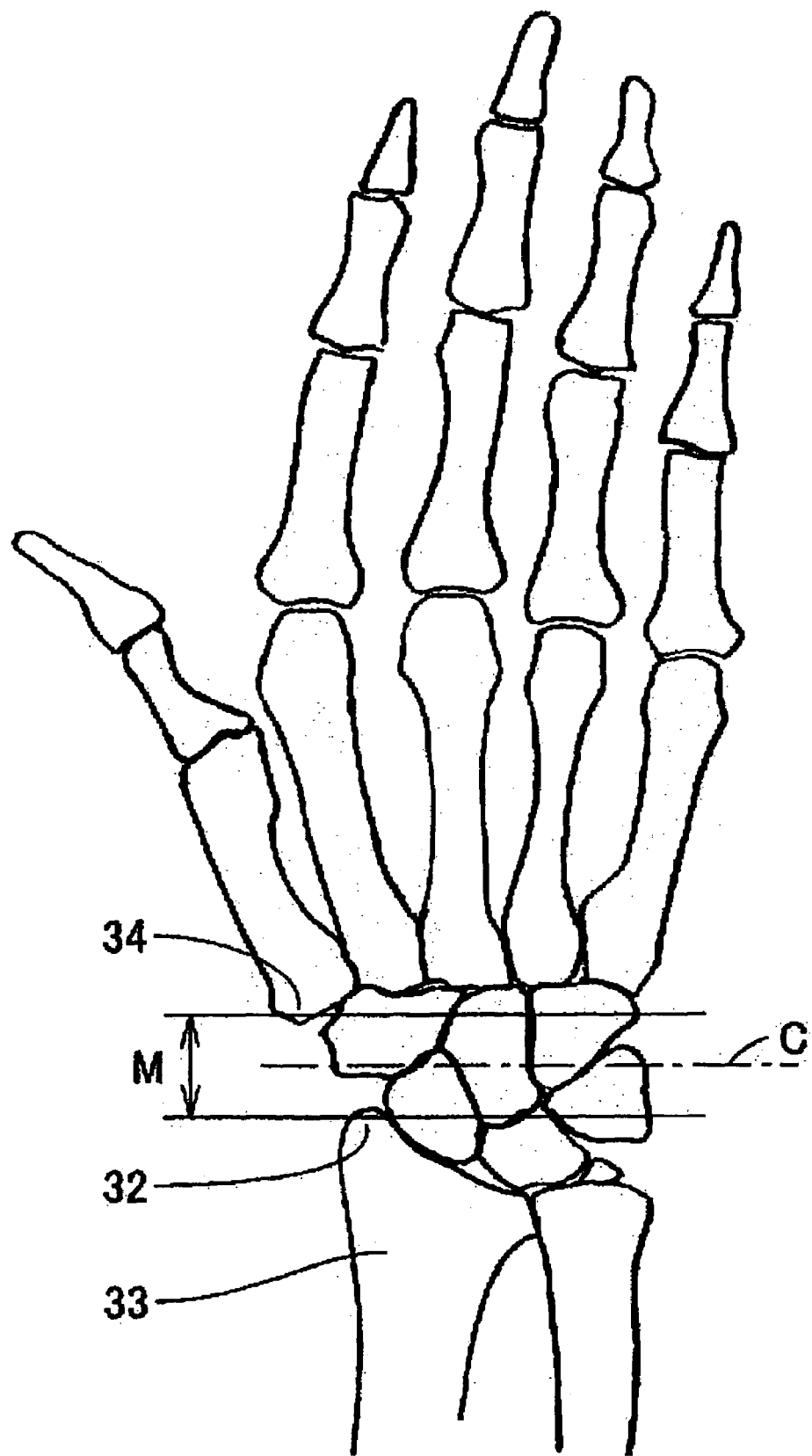
FIG. 5 shows a top plan view of a skeleton of a wrist describing a mounting position of a blood pressure meter cuff in a second embodiment based on the invention.
Figure 6:
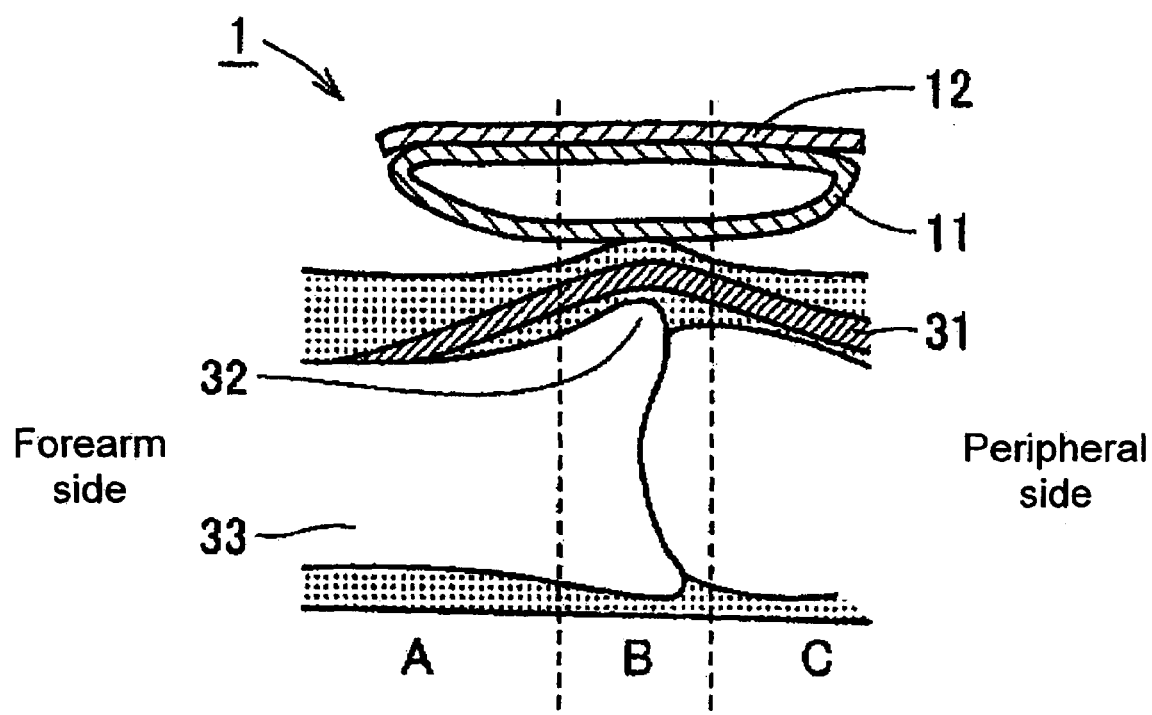
FIG. 6 shows a sectional view of a state where a conventional blood pressure meter cuff is mounted on a wrist.

Description will be given of the second embodiment focusing on only matters different from the above embodiment with reference to FIG. 5. Note that FIG. 5 is a top plan view of a skeleton of a wrist as viewed from the palm side.

In the above embodiment, the cuff 1 is designed so as to be suitable for pressurizing the radial artery 31 in the downward vicinity of the body surface and above the radial styloid process 32. In this embodiment, the cuff 1 is designed so as to be suitable for pressurizing the radial artery present in the downward vicinity of the body surface in an intermediate portion M between the radial styloid process 32 and the first metacarpal bone base 34 as shown in FIG. 5.

According to experiments conducted by the inventors, in a case of the radial artery, it has been confirmed that a pulse wave can be sensed most stably at a position spaced to the peripheral side from the top from the top of the radial styloid process 32 by a distance in the range of from about 5 to about 15 mm therefrom. The position is on the center line C of a wrist joint. The position can also be specified as a position between the radial styloid process 32 and the first metacarpal bone base 34 just bisecting a distance therebetween.

The inventors confirmed reproducibility in measurement by rewrapping the cuff 1 plural times and has found that that the fluid bag 11 is brought into contact with the bisecting point between the radial styloid process 32 and the first metacarpal bone base 34 makes it possible to measure a stabler blood pressure measurement without error as compared with that the fluid bag 11 is brought into contact with a portion of the skin right above the radial styloid process 32.

The reasons therefor are considered such that the radial artery 31 is not necessarily at the shallowest position under the skin near the top of the radial styloid process 32 and that stabler pressurization can be realized in a portion between the radial styloid process 32 and the first metacarpal bone base 34 than in a portion right above the radial styloid process 32 since the radial artery in the intermediate portion is harder to be displaced in terms of an anatomical structure than a portion of the skin right above the top of the radial styloid process 32.

In this embodiment, a width W, in the axial direction of a limb, of the fluid bag 11 of the cuff 1 is set to a value of 15 mm or more and 25 mm or less so as to be suitable for such a use condition.

In the above two embodiments, constructions are designed so as to pressurize only the radial artery present in the downward vicinity of the body surface in a wrist section. A blood pressure meter cuff of the invention may be designed so as to pressurize another artery present in the downward vicinity of the surface of a limb of a human body. For example, a construction may also be adopted in which pressurization is conducted on only a portion of an ulnar artery in the downward vicinity of the body surface or in which pressurization is imposed simultaneously on portions of a radial artery and ulnar artery in the downward vicinity of the body surface.

It should be understood that the embodiments disclosed above are presented by way of illustration but not by way of limitation in every respects. The technical scope of the invention is defined based on the terms of the appended claims without being interpreted only by the embodiments and includes all alterations and modifications of the embodiments without departing from the technical scope and the equivalent thereof.

According to a blood pressure meter of the invention, it is possible to pressurize a blood vessel present in the downward vicinity of the skin. As a result, a correct measurement on a blood pressure can be realized without receiving an influence of the cuff edge effect.

The invention claimed is:

1. A method for measuring blood pressure, comprising:
   fixing a fluid bag for receiving an injected fluid on a limb of a subject at a location on the limb;
   inflating the fluid bag, to cause the fluid bag to selectively pressurize only a portion of a radial artery present in the downward vicinity of a body surface and in an intermediate portion between a radial styloid process of a wrist of the subject and a first metacarpal bone base thereof without pressurizing an ulnar artery of the wrist; and
   measuring blood pressure with using the fluid bag.

2. The method of claim 1, further comprising sensing a pulse wave at a position between about 5 mm to 15 mm from a top of the radial styloid process.

3. The method of claim 1, further comprising sensing a pulse wave at a position at about the midpoint of a distance between the radial styloid process and the first metacarpal bone base.

4. The method of claim 1, further comprising sensing a pulse wave at a position to a peripheral side of the radial styloid process.

* * * * *